United States Patent
Parmeter et al.

(10) Patent No.: US 6,848,325 B2
(45) Date of Patent: Feb. 1, 2005

(54) EXPLOSIVES SCREENING ON A VEHICLE SURFACE

(75) Inventors: John E. Parmeter, Albuquerque, NM (US); Charles A. Brusseau, Tijeras, NM (US); Jerry D. Davis, Albuquerque, NM (US); Kevin L. Linker, Albuquerque, NM (US); David W. Hannum, Albuquerque, NM (US)

(73) Assignee: Sandia Corporation, Albuquerque, NM (US)

(*) Notice: Subject to any disclaimer, the term of this patent is extended or adjusted under 35 U.S.C. 154(b) by 0 days.

(21) Appl. No.: 09/826,502

(22) Filed: Apr. 4, 2001

(65) Prior Publication Data

US 2004/0055399 A1 Mar. 25, 2004

(51) Int. Cl.[7] ............................................... G01N 1/00
(52) U.S. Cl. ................................................... 73/864.33
(58) Field of Search ........................ 73/864.33, 864.71, 73/863.21, 863.22, 863.23, 863.24, 864.81, 864.83

(56) References Cited

U.S. PATENT DOCUMENTS

| | | | |
|---|---|---|---|
| 3,748,905 A | * 7/1973 | Fletcher et al. | 73/863.25 |
| 4,712,339 A | 12/1987 | Wenham et al. | 52/173 |
| 4,909,090 A | 3/1990 | McGown et al. | 73/864.33 |
| 4,987,767 A | * 1/1991 | Corrigan et al. | 73/23.36 |
| 5,098,640 A | 3/1992 | Gozani et al. | 376/166 |
| 5,124,554 A | 6/1992 | Fowler et al. | 250/358.1 |
| 5,476,794 A | 12/1995 | O'Brien et al. | 436/92 |
| 5,592,083 A | 1/1997 | Magnuson et al. | 324/300 |
| 5,915,268 A | 6/1999 | Linker et al. | 73/23.2 |
| 5,939,647 A | * 8/1999 | Chinn et al. | 73/864.71 |
| 6,067,167 A | * 5/2000 | Atkinson et al. | 356/437 |
| 6,085,601 A | * 7/2000 | Linker et al. | 73/863.12 |
| 6,408,701 B1 | * 6/2002 | Fujita | 73/864.71 |
| 6,446,514 B1 | * 9/2002 | Danylewych-May et al. | 73/863.21 |

OTHER PUBLICATIONS

US5592083: System and method for contaband detection using nuclear quadrupole resonance including a sheet coil and RF shielding via waveguide below, downloaded from www.delphion.com. Jan. 2001.
US5124554: Explosive detector, downloaded from www.delphion.com. Jan. 2001.

* cited by examiner

Primary Examiner—Robert Raevis
(74) Attorney, Agent, or Firm—George Libman

(57) ABSTRACT

A system for detecting particles on the outer surface of a vehicle has a housing capable of being placed in a test position adjacent to, but not in contact with, a portion of the outer surface of the vehicle. An elongate sealing member is fastened to the housing along a perimeter surrounding the wall, and the elongate sealing member has a contact surface facing away from the wall to contact the outer surface of the vehicle to define a test volume when the wall is in the test position. A gas flow system has at least one gas inlet extending through the wall for providing a gas stream against the surface of the vehicle within the test volume. This gas stream, which preferably is air, dislodges particles from the surface of the vehicle covered by the housing. The gas stream exits the test volume through a gas outlet and particles in the stream are detected.

10 Claims, 3 Drawing Sheets

EXPLOSIVES SCREENING ON A VEHICLE SURFACE

The United States Government has rights to this invention pursuant to Department of Energy Contract No. DE-AC04-94AL85000 with Sandia Corporation.

BACKGROUND OF THE INVENTION

Screening for explosives at checkpoints is a high priority for a number of Government agencies. Depending on the checkpoint, this screening can involve the search of people, hand-carried items, shipped or mailed items, and vehicles. Of these, the screening of vehicles for explosives is the most difficult due to the number of places that explosives may be hidden in a vehicle, and very important due to the large amount of explosives that may be carried in a vehicle.

Current methods of screening vehicles for explosives includes physical search by people, the use of trained animals (such as dogs), x-ray portals, portals based on nuclear technologies, and surface swipes. Each of these methods has significant limitations.

Physical search by trained people requires little equipment, but has high labor costs. It is also quite slow and likely to miss explosives hidden within body panels or buried in large loads. The physical search is most useful as a follow-up to verify or disprove an indication of explosives by one of the other methods.

The use of trained dogs is effective and relatively quick, but dogs have a durability problem in that they require breaks every couple of hours, and they require a handler, which is a high labor cost. They would not be acceptable at a high-traffic checkpoint, although they are very useful as a backup to an automated inspection system.

An x-ray portal can see behind panels and into tires; a great advantage in detection. However, these portals are very expensive and require the occupants to leave the vehicle while it is under test. A typical inspection would also be too slow for a high traffic checkpoint. Furthermore, operator interpretation is normally required to determine whether an explosive may be present. This limitation is significant, since large quantities of explosives may produce an image that is indistinguishable from an innocuous object.

The surface swipe involves an operator passing a clean swab or other collection medium over a vehicle surface, and then doing an on-site inspection for explosive particles that may have been collected by the medium. The surface swipe is not automated, so it has high labor costs; however, equipment costs are relatively moderate.

There are several types of nuclear detection systems. Typical systems include U.S. Pat. No. 5,124,554 of P. Fowler et al., *Explosives Detector*, which discloses a thermal neutron activation system based on the interaction of neutrons with nitrogen atoms in explosives. U.S. Pat. No. 5,098,640 of T. Gozani et al., *Apparatus and Method for Detecting Contraband Using Fast Neutron Activation*, discloses a technique based on the interaction of neutrons with explosive material, which results in the emission of gamma rays with characteristics that are indicative of the specific material. And U.S. Pat. No. 5,592,083 of E. Magnuson et al., *System and Method for Contraband Detection Using Nuclear Quadrupole Resonance Including a Sheet Coil and RF Shielding via Waveguide Below Cutoff*, uses nuclear quadrupole resonance excited by an RF signal to detect explosives. These systems are usually somewhat less expensive than x-ray equipment, but they are still not fast enough for heavy traffic checkpoints and they may suffer from false alarms caused by common materials. Also, quadrupole resonance may not be useful in vehicle screening applications due to the shielding effect of a metal vehicle body.

A relatively new technology that is being tested for detection of explosives on people is disclosed in U.S. Pat. No. 5,915,268 of K. Linker et al., Vertical Flow Chemical Detection Portal, which patent is owned by the assignee of this invention. This patent discloses an open-sided portal in which a flow of air is directed vertically over a person in the portal, and horizontal jets help dislodge particles from the person's body. The air is passed through a concentration apparatus to an ion mobility spectrometer for detection and identification of trace explosives.

One of the positive features of the portal detector is that trace explosives detected by this system do not occur naturally, and cleansing of detectable particles from a person or object that contacted explosives is not a trivial matter. Accordingly, if an automatic portal detector provides a positive indication, it may not mean that the object or person is presently carrying explosives, but it is a very reliable indication that they were recently in contact with explosives, and are a logical target for a search by trained people.

Although, conceptually, this desirable portal technology could be adapted to vehicles by having a larger drive-through portal, the amount of air movement that would be required to analyze a typical automobile would be very large, and implementation would require a garage or similar structure, making the device impractical to move.

SUMMARY OF THE INVENTION

It is an object of this invention to detect automatically explosive material such as particles on a vehicle or vapor from the vehicle relatively quickly and accurately, and without requiring occupants to leave the vehicle.

It is a further object of this invention to provide a modification of the portal technology to operate on a portion of the outer surface of a vehicle to detect explosive material.

To achieve the foregoing and other objects, and in accordance with the purpose of the present invention, as embodied and broadly described herein, the present invention may comprise a system for detecting particles on the outer surface of a vehicle comprising a housing including a wall capable of being placed in a test position adjacent to, but not in contact with, a portion of the outer surface of the vehicle. An elongate sealing member is fastened to the housing along a perimeter surrounding said wall, and the elongate sealing member has a contact surface facing away from the wall to contact the outer surface of the vehicle to define a test volume when the wall is in the test position. A gas flow system has at least one gas inlet extending through the wall for providing a gas stream against the surface of the vehicle within the test volume. This gas stream, which preferably is air, dislodges particles from the surface of the vehicle covered by the housing. The gas stream exits the test volume through a gas outlet and particles in the stream are detected. Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

The basis for this invention is the realization that a vehicle carrying explosives will often have trace explosives on predictable locations of the outer surface of the vehicle.

Figure 1:
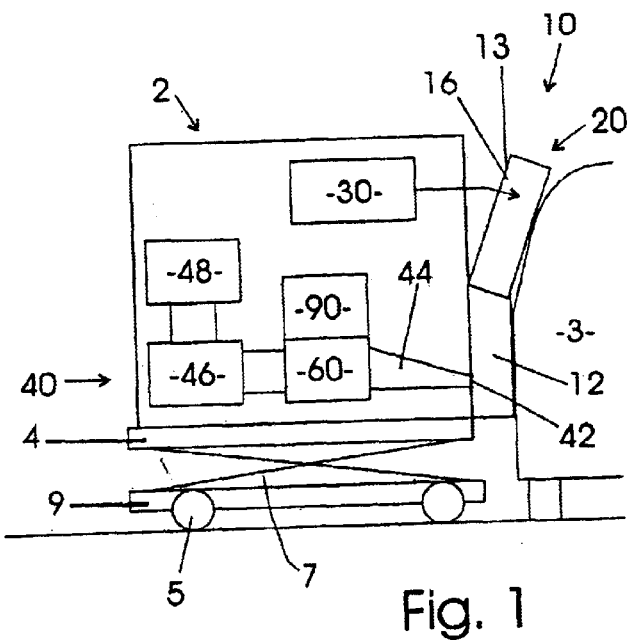
FIG. 1 shows a particle detector in accordance with this invention against a portion of a vehicle.

In accordance with a system 1 of this invention, FIG. 1 discloses a frame 2 resting on a subframe 4 and a base 9. A housing 10 is mounted at one end of frame 2. Conventional means are provided for enabling frame 2 to be moved in the direction of housing 10 (defined as 'forward', or toward a vehicle 3 to be tested) or in the direction away from housing 10 (defined as 'backward', or away from the vehicle to be tested). In the simplest embodiment, these means could be skids or wheels 5 on base 9, and a force applied by mechanical, human, or other means to move frame 2 in the desired direction. Conventional lift apparatus, such as scissors jack 7, are provided to adjust the height of subframe 4 relative to base 9 for proper placement of housing 10 against vehicle 3.

Housing 10 is designed to fit against the portion of a vehicle body to be tested for particles. Housing 10 includes a wall 13 that faces and is spaced from vehicle 3 by a sealing member 20. As discussed hereinafter, housing 10 may be divided into two hinged parts, lower housing 12 and upper housing 16. This hinged construction permits housing 10 to conform more closely to the irregular surface of vehicle 3 than would a planar housing.

Frame 2 includes a gas input system 30 for providing gas under pressure to housing 10 where the gas is directed against the surface of vehicle 3 to dislodge particles to be detected. The gas is preferably air, which requires only a compressor or equivalent means for supplying air under pressure to housing 10, but other gases such as nitrogen or noble gases could be stored under pressure and supplied to housing 10 if air would be undesirable for the detection process.

Sealing member 20 forms a flexible barrier between wall 13 and vehicle 3 to enclose a test volume and keep most of the gas, which dislodges particles from vehicle 3 within the test volume. An outlet 42, which outlet is the input to a gas output system 40, is provided from housing 10. Gas output system 40 may include ductwork 44 leading to a particle detection system 60, which system may comprise a particle preconcentrator 62 and a trace chemical detector 90, as discussed hereinafter. A blower or equivalent gas moving device 46 applies a negative pressure to outlet 42 to draw gas and particles from the test volume through detection system 60. A noise muffler 48 may be used on the exhaust or output of gas moving device 46.

Figure 2:
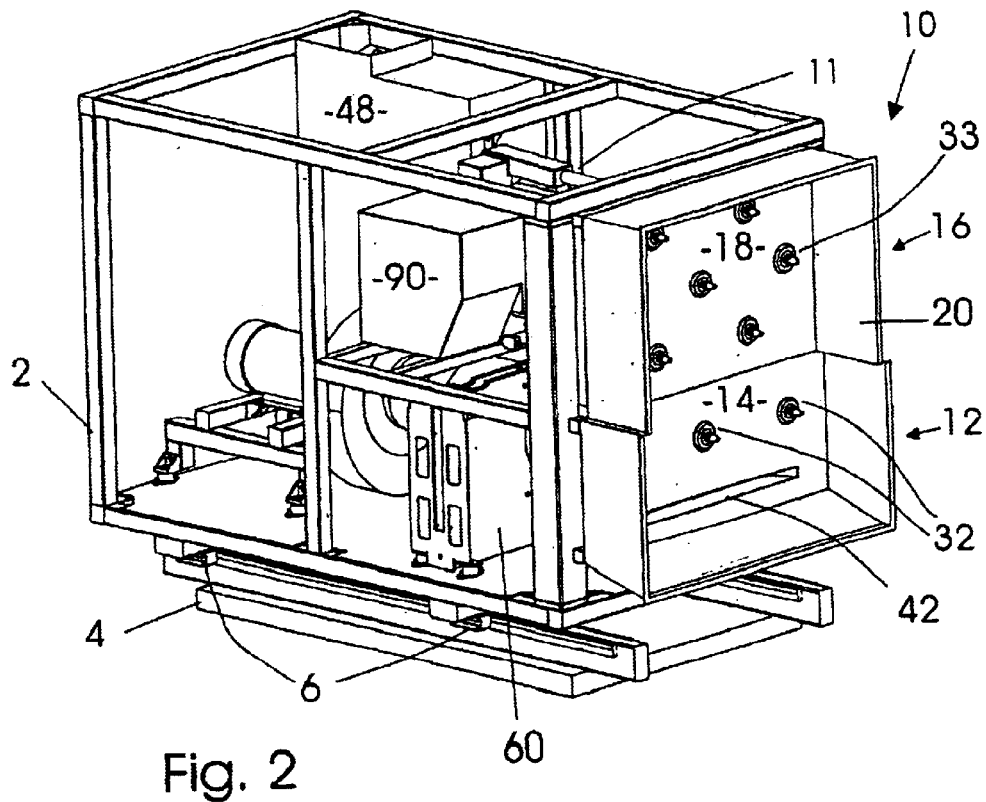
FIG. 2 shows a partial cut-away oblique front view of an embodiment of the invention.
Figure 3:
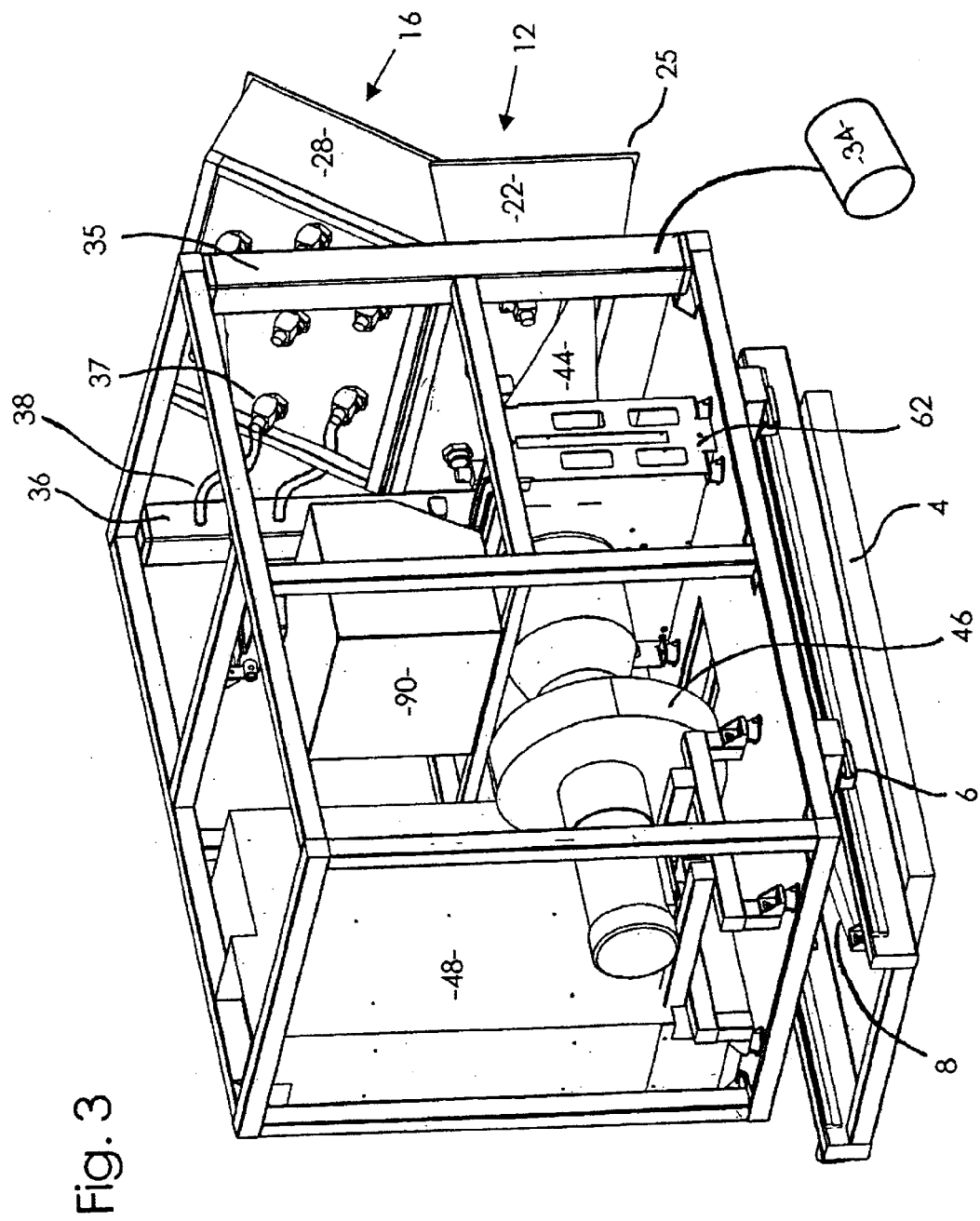
FIG. 3 shows an oblique back view of the embodiment of FIG. 1.

A preferred embodiment of the invention is shown in FIGS. 2 and 3. In this embodiment, the means for moving frame 2 include a subframe 4 and a plurality of glides 6 (two on each side), which support frame 2 and provide a low-friction interface between frame 2 and subframe 4. An actuator 8, for example, a screw drive or equivalent device for extending or retracting a mechanical connection, is attached between subframe 4 and frame 2 to position frame 2 forward for a test, or backward to permit a vehicle to move in or out of position to be tested. A second actuator 11 connected between frame 2 and upper housing 16 controls the angle of upper housing 16 relative to lower housing 12.

Two piece housing 10 is seen in FIGS. 2 and 3 to include lower housing 12 which is affixed to the front of frame 2, and upper housing 16 which is hinged at its lower edge to an upper edge of lower housing 12. Lower housing 12 includes a lower wall 14 which has elongated gas outlet 42 for gas to exit the test volume, and a plurality of gas inlet nozzles 32. Upper housing 16 includes an upper wall 18 that has additional gas inlet nozzles 33 in three rows. The number and arrangement of gas inlet nozzles is a matter of design choice as long as a sufficient number and distribution are provided to cover the portion of the surface of vehicle 3 to be tested.

Gas system 30 includes connections and a gas supply that is partially illustrated in the embodiment of FIGS. 2 and 3. A compressor 34 or other conventional source of gas under pressure provides gas such as air to pressurized storage chambers 35, 36, which chambers conveniently also function as vertical members at the front of frame 2. A flexible hose 38 extends from either of storage chambers 35, 36 to each nozzle 32, 33.

Conventional controls are utilized to control the flow of gas through nozzles 32, 33. For example, an electronically controlled valve 37 could be at either end of each hose 38. Such a configuration is preferable for individual control of the flow from each nozzle. Alternatively, if all nozzles are to be controlled simultaneously, a single-input, many-output manifold (not shown) could be placed between the output of each gas storage chamber 35, 36 and hoses 38. A single valve at the input to each manifold would control the flow through all the nozzles connected to that manifold. Other arrangements for connecting nozzles 32 to the gas supply, and controlling the flow of gas through the nozzles, are also contemplated.

Sealing member 20 may be a rim of elastic material such as plastic which has one edge 25 which contacts vehicle 3 and an opposed edge that is fastened to housing 10. For the two-part housing of FIGS. 2 and 3, sealing member 20 has an upper member 28 which surrounds the upper three sides of upper wall 18, and a lower member 22 which surrounds the lower three sides of lower wall 12.

Sealing member 20 performs the function of forming a barrier to enclose a test volume and thereby direct the particles dislodged from the surface of vehicle 3 through outlet 42. While, ideally, sealing member 20 forms an air-tight seal with the surface of vehicle 3, practically, it is sufficiently pliable to conform to the surface of vehicle 3 and form a barrier that resists the escape of gas from the test volume. For one test of the invention, sealing member 20 was formed of 3.5 inch foam rubber bulb boot material that conventionally is used between the bed and cab of a pickup truck. Since gas output system 40 maintains a negative pressure at test volume outlet 42, gas from inlets 32,33, and particles carried thereby, naturally flow through outlet 42 for further processing. The barrier also ensures that minimal outside air is drawn into the test volume through openings between sealing member edge 25 and vehicle 3. However, if housing 10 is placed over a vehicle door, and the window of that door is cracked open, the negative pressure in the test volume will also draw air from the vehicle into the system, which enhances the probability that particles or vapors from the interior of the vehicle will also be detected.

Since the concentration of particles to be detected in the air flowing through outlet 42 is quite small, detection system 60 preferably includes a preconcentrator 62 mounted between the output of ductwork 44 and blower 46 to increase the concentration of explosives for more reliable detection by detector 90. An example of a preconcentrator 62 which may be utilized in this invention is disclosed in U.S. Pat. No. 5,854,431 of K. Linker, which patent is incorporated herein by reference. The details of this preconcentrator are not illustrated here, but it has a metal felt screen which filters explosive material from gas flowing through it. After a gas sample has passed through the screen, the flow is stopped and the screen is electrically heated to release the trapped material. A transverse gas stream from a secondary source then blows across the screen to move the material with a much smaller gas stream into a detector such as an ion mobility spectrometer 90. Preferably, preconcentrator 62 is an improved two-stage preconcentrator as disclosed in pending application Ser. No. 09/594,215 of K. Linker et al, filed Jun. 14, 2000, which application is also incorporated herein by reference. Whereas the diameter of the screen in ductwork 42 is on the order of 6 to 9 inches, the two-stage preconcentrator has a second stage with a second screen having a diameter on the order of less than 1 inch. Explosive material from the first screen is deposited on the second screen, and another lower pressure gas stream then moves the material to the detection device. The gas flow at the output of the two-stage preconcentrator matches the gas requirements of a spectrometer better than the single stage preconcentrator of the '215 patent, resulting in improved detection.

The concentration of material by this device is evident from the fact that if 1500 liters of air pass through the $1^{st}$ stage of preconcentrator 60 while the vehicle is being exposed to the air flow in the test volume, most of the trapped material is moved to the $2^{nd}$ stage of preconcentrator 60 by a flow of 13 liters of air, and most of this trapped material is moved to the detector by a flow of 0.025 liters of air. Therefore, while the amount of material reaching the detector may have been reduced by an estimated factor of 2 due to losses in the two preconcentrator stages, the air flow carrying this material has been reduced by a factor of $6 \times 10^4$, resulting in a much higher concentration of material at the detector, which concentration significantly increases the likelihood that trace explosives in the gas flow will be detected.

Alternative arrangements for ensuring that the air from nozzles 30 does not escape the system are also contemplated in the practice of this invention. For example, one of ordinary skill in the art could form housing 10 of either one or three or more sections, depending on the variety of vehicle bodies to be tested. Furthermore, sealing member 20 could be replaced by a flexible bellows of the type utilized at the end of airport walkways which move into contact with aircraft, as exemplified by U.S. Pat. No. 4,712,339 of B. Wenham et al. Such a sealing member could extend from frame 2 and surround, but not be affixed to, housing 10. Air curtains formed by a series of nozzles surrounding housing 10 and pointing at vehicle 3 could also be used to define a test volume for this invention.

Figure 4:
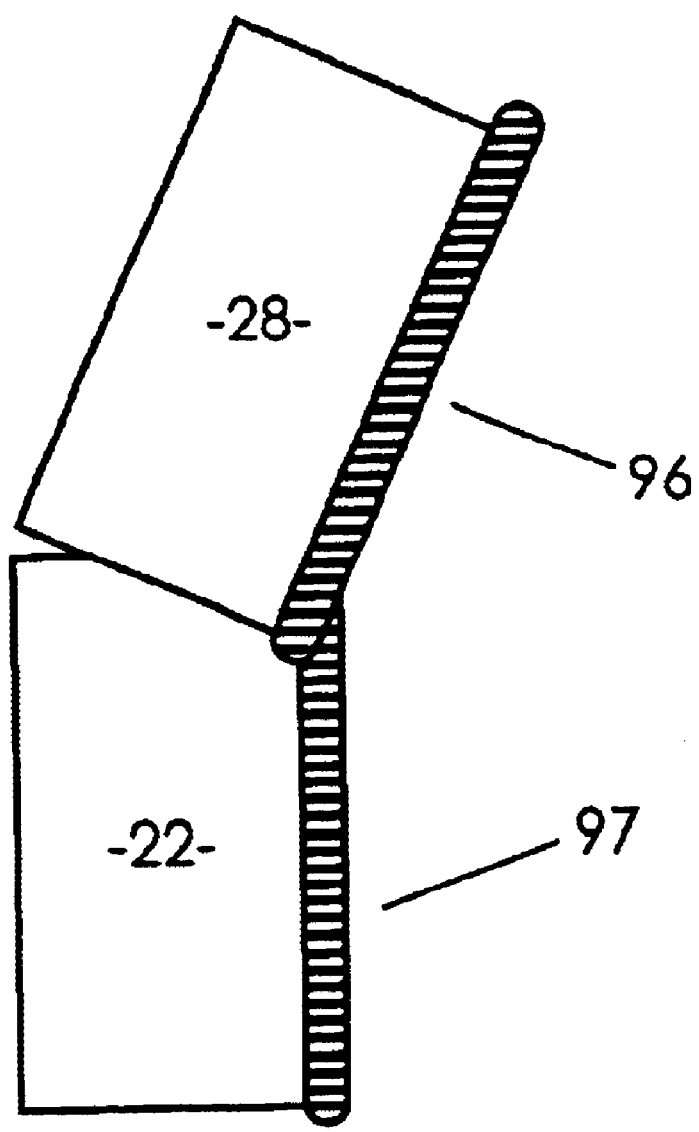
FIG. 4 shows a side view of the embodiment of FIG. 1, including bellows.

FIG. 4 shows a side view of the embodiment of FIG. 1, illustrating bellows 96 and 97 attached to upper and lower members 28 and 22, respectively.

The operation of this system is somewhat similar to the operation of the aforementioned portal detector of U.S. Pat. No. 5,915,268. A vehicle 3 is stopped at a position spaced from the front of frame 2, which frame is moved forward and upward (if necessary) to put housing 10 adjacent to the portion of vehicle 3 to be tested. Housing 10 and sealing member 20 are then moved into a test position over a portion of the surface of vehicle 3, forming a test volume including wall 12, sealing member 20 and the vehicle surface. Gas, preferably air, is then provided at relatively high pressure through nozzles 32, 33 against vehicle surface 3 to dislodge any explosive particles which may be on that surface. Gas moving device 46 is also energized, setting up a gas flow from nozzles 30 through ductwork 42, and explosive material is filtered from the gas flow by preconcentrator 62. After gas has flowed for a sufficient period of time, which period is typically on the order of a few minutes, the gas flow is stopped and the particles are transported from preconcentrator 62 to detector 90 as discussed in the aforementioned preconcentrator patents. The total time for a test to provide an indication of whether or not explosive particles are present is about five minutes. At the conclusion of the test, the housing and frame are withdrawn, and the vehicle may move away from the system.

The invention may be constructed of common materials, but those components which contain the gas flow, such as housing wall 12, sealing member 20, and ductwork 42, are preferably materials such as stainless steel and which do not naturally attract explosive particles, as the intent of the system is that such particles are moved to detector 90, and not retained in the system.

The amount of pressure that is necessary to dislodge particles, and the optimum time necessary for gas flow to provide a reliable indication of explosive particles in the gas stream, is a function of the particular housing structure and vehicle shape that may be readily determined by controlled experiments. It is contemplated that different vehicle shapes may require different pressures and/or flow times.

The particular sizes and equipment discussed above are cited merely to illustrate a particular embodiment of this invention. It is contemplated that the use of the invention may involve components having different sizes and shapes as long as the principle of flowing gas over a vehicle surface to disclosed explosive particles, which are carried to a detector, is followed. It is intended that the scope of the invention be defined by the claims appended hereto.

What is claimed is:

1. A system for detecting particles on a vehicle having an outer surface comprising:

a housing including
    a wall capable of being placed in a test position adjacent to, but not in contact with, a portion of the outer surface of the vehicle; and
    an elongate sealing member fastened to said housing along a perimeter surrounding said wall, said elongate sealing member having a contact surface facing away from said wall, said contact surface contacting the outer surface of the vehicle to define a test volume when said wall is in said test position;
a gas flow system comprising
    at least one gas inlet extending through said wall for providing a gas stream against the surface of the vehicle within the test volume;
    a gas outlet for gas to exit the test volume; and
detector means for detecting the presence of particles in the gas passing through said gas outlet;
wherein said sealing member comprises a hollow bellows having one end extending along the perimeter and an opposing end;

said housing further comprising activating means for moving said opposing end of said bellows against the outer surface of the vehicle.

2. The system of claim 1 wherein said wall is movable, and said housing further comprises means for moving said wall to conform to the contour of the portion of the outer surface of the vehicle.

3. The system of claim 2 wherein said housing and said wall consist of upper and lower parts hinged at their intersection, wherein said upper part is adjusted relative to said lower part to conform to the vehicle surface.

4. The system of claim 1 wherein said sealing member comprises a continuous band of thin, flexible material, said band having one edge extending along the perimeter and an opposing edge for contacting and conforming to the vehicle surface.

5. The system of claim 1 wherein said gas flow system comprises a plurality of gas inlets distributed on said wall, wherein the gas stream impinges substantially the entire surface of the vehicle opposite said wall.

6. The system of claim 5 wherein said gas outlet extends across the lower portion of said wall.

7. The system of claim 1 wherein said gas flow system further comprises a confined path for gas exiting the test volume; and said detector means has an input port for receiving all gas passing through said confined path and an output port.

8. The system of claim 7 wherein said gas flow system further comprises means for applying a lower gas pressure to said output port of said detector than is on said input port of said detector, whereby gas from the test volume is drawn through said gas outlet to said detector.

9. The system of claim 8 wherein said sealing means completely surrounds said wall.

10. The system of claim 7 wherein said detector means comprises a particle collection device having said input port, and a particle detector for determining if particles are present in said collection device.

* * * * *